(12) United States Patent
Thoe

(10) Patent No.: US 6,962,581 B2
(45) Date of Patent: Nov. 8, 2005

(54) FOOT CONTROLLER FOR MICROSURGICAL SYSTEM

(75) Inventor: David A. Thoe, Aliso Viejo, CA (US)

(73) Assignee: Alcon, Inc., Hunenberg (CH)

( * ) Notice: Subject to any disclaimer, the term of this patent is extended or adjusted under 35 U.S.C. 154(b) by 68 days.

(21) Appl. No.: 10/308,498

(22) Filed: Dec. 3, 2002

(65) Prior Publication Data

US 2004/0106915 A1 Jun. 3, 2004

(51) Int. Cl.⁷ .............................. A61B 17/00
(52) U.S. Cl. ........................ 606/1; 200/51.02
(58) Field of Search .................... 606/1; 200/51.02, 200/51, 51.05, 86.5

(56) References Cited

U.S. PATENT DOCUMENTS

| | | |
|---|---|---|
| 4,168,707 A | 9/1979 | Douvas et al. |
| 4,274,411 A | 6/1981 | Dotson, Jr. |
| 4,837,857 A | 6/1989 | Scheller et al. |
| 4,983,901 A | 1/1991 | Lehmer |
| 5,091,656 A | 2/1992 | Gahn |
| 5,157,603 A | 10/1992 | Scheller et al. |
| 5,268,624 A | 12/1993 | Zanger |
| 5,342,293 A | 8/1994 | Zanger |
| 5,403,276 A | 4/1995 | Schechter et al. |
| 5,554,894 A | 9/1996 | Sepielli |
| 5,580,347 A | 12/1996 | Reimels |
| 5,810,765 A | 9/1998 | Oda |
| 5,983,749 A | 11/1999 | Holtorf |
| 6,055,458 A | 4/2000 | Cochran et al. |
| 6,117,126 A | 9/2000 | Appelbaum et al. |
| 6,149,621 A | 11/2000 | Makihara |
| 6,179,829 B1 | 1/2001 | Bisch et al. |
| 6,452,120 B1 | 9/2002 | Chen |
| 6,452,123 B1 | 9/2002 | Chen |
| 6,674,030 B2 | 1/2004 | Chen et al. |

FOREIGN PATENT DOCUMENTS

| | | |
|---|---|---|
| EP | 0 789 929 | 7/2002 |
| WO | WO 96/13845 | 5/1996 |
| WO | WO 98/08442 | 3/1998 |
| WO | WO 99/14648 | 3/1999 |
| WO | WO 00/12037 | 3/2000 |
| WO | WO 01/86369 | 11/2001 |

OTHER PUBLICATIONS

Japanese Patent Abstract; Publication No. 2000–229102, Aug. 22, 2000.

Primary Examiner—Rosiland Rollins
(74) Attorney, Agent, or Firm—W. David Lee

(57) ABSTRACT

An improved foot controller of a microsurgical system, and a method of operating the foot controller, are disclosed. The method involves using a computer to modulate a detent of the foot controller from the beginning of the detent to the end of the detent.

12 Claims, 4 Drawing Sheets

US 6,962,581 B2

FOOT CONTROLLER FOR MICROSURGICAL SYSTEM

FIELD OF THE INVENTION

The present invention generally pertains to foot controllers used in the operation of microsurgical systems. The present invention more particularly pertains to an improved, surgeon definable detent for such foot controllers.

DESCRIPTION OF THE RELATED ART

Various foot controllers are used to control microsurgical systems, and particularly ophthalmic microsurgical systems. During ophthalmic surgery, a surgeon views the patient's eye through an operating microscope. To control the microsurgical system and its associated handpieces during the various portions of the surgical procedure, the surgeon must either instruct a nurse how to alter the machine settings on the surgical system, or use the foot controller to change such settings. Where possible, many surgeons prefer to use the foot controller to alter the machine settings on the surgical system, eliminating or reducing the need to converse with a nurse during the surgical procedure.

Many conventional foot controllers have a foot pedal that provides linear control of the functions of the surgical system or an associated handpiece, and a series of switches or buttons that provide binary control of such functions. Exemplary foot controllers for ophthalmic microsurgical systems are disclosed in International Publication Number WO 00/12037; International Publication Number WO 99/14648; International Publication Number WO 98/08442; International Publication No. WO 96/13845; U.S. Pat. Nos. 5,983,749; 5,580,347; 4,837,857; 4,983,901; 5,091,056; 5,268,624; 5,554,894, all of which are incorporated herein by reference.

Such foot controllers typically have a foot pedal that is capable of movement by the surgeon in a given range of motion. This range of motion is typically segregated into several areas, each of which controls a different surgical mode. For example, moving a foot pedal into a first area may provide a fixed amount of irrigation flow to a phacoemulsification handpiece. Moving the foot pedal into a second area may provide fixed irrigation flow and linear control of aspiration flow to the handpiece. Moving the foot pedal into a third area may provide fixed irrigation flow, linear control of aspiration flow, and linear control of ultrasound power to the handpiece. Each of these areas is typically separated by a relatively small range of foot pedal travel (and/or a small amount of time) in which the surgeon feels increased resistance against his or her foot as it presses on the pedal. These small ranges of foot pedal travel are typically referred to as detents. The increased resistance felt by a surgeon's foot as the foot pedal passes through a detent is typically provided by an increase in torque generated by the detent motor of the foot controller that opposes the force of the surgeon's foot on the foot pedal. Once the surgeon moves the pedal through a detent, the resistance felt by the surgeon's foot decreases. U.S. Pat. Nos. 4,983,901; 4,168,707; 5,091,656; 6,179,829; and European Patent No. 0 789 929 B1, all of which are incorporated herein by reference, disclose examples of such detents.

However, conventional foot controllers suffer from the disadvantage that the force necessary to overcome a detent and move to the next surgical mode results in the foot pedal having a somewhat stiff feeling to the surgeon. If the force required to overcome the detent is decreased in amplitude to reduce such stiffness, the detent becomes difficult for the surgeon to detect. Therefore, a need still exists for an improved detent in foot controllers used in the operation of microsurgical systems.

SUMMARY OF THE INVENTION

In one aspect, the present invention is an improved method of operating a foot controller of a microsurgical system. A microsurgical system having a computer and a foot controller operatively coupled to the computer is provided. The foot controller has a foot pedal with a range of motion. The range of motion has a first area indicative of a first surgical mode of the microsurgical system and a second area indicative of a second surgical mode of the microsurgical system. The first and second areas are separated by a detent. The computer is used to modulate the detent by varying a resistance felt by a user's foot as it presses on the foot pedal. The varying of the resistance may occur at a given frequency from the beginning of the detent to an end of the detent.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 8 of the drawings, like numerals being used for like and corresponding parts of the various drawings.

Figure 1:
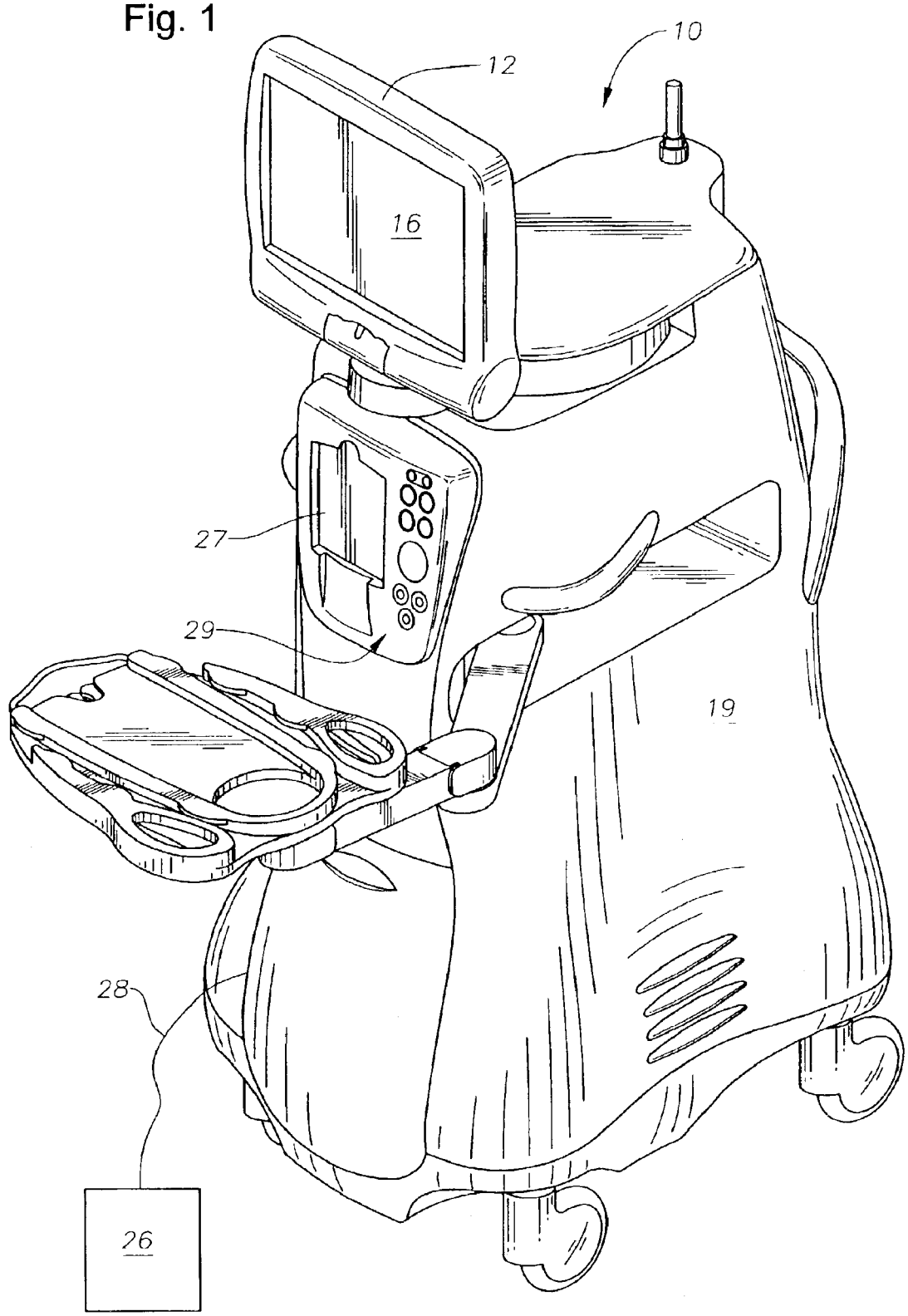
FIG. 1 is a perspective view of a microsurgical system according to a preferred embodiment of the present invention.
Figure 2:
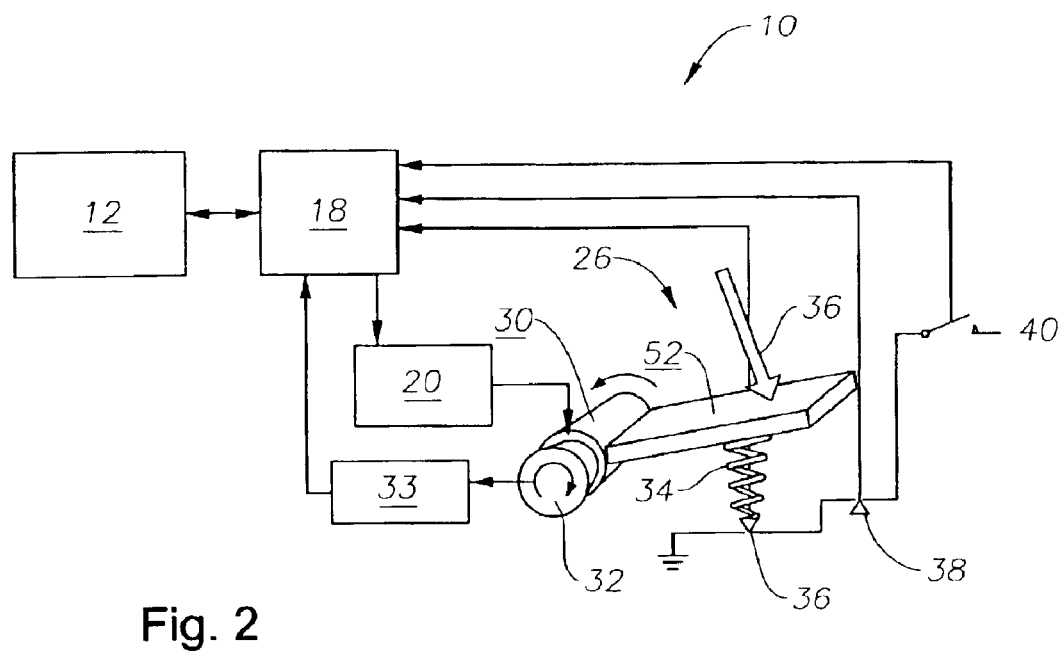
FIG. 2 is a block diagram of certain portions of the microsurgical system of FIG. 1 and its associated foot controller according to a preferred embodiment of the present invention.

FIGS. 1–2 show a microsurgical system 10 according to a preferred embodiment of the present invention. As shown in FIG. 1, microsurgical system 10 is an ophthalmic microsurgical system. However, microsurgical system 10 may be any microsurgical system, including a system for performing otic, nasal, throat, or other surgeries. System 10 is capable of providing ultrasound power, irrigation fluid, and aspiration vacuum to a ultrasonic handpiece in an anterior segment ophthalmic surgical procedure. System 10 may also be capable of providing pneumatic drive pressure and aspiration vacuum to a vitrectomy probe and irrigation fluid to an infusion cannula in a posterior segment ophthalmic surgical procedure. System 10 preferably includes a graphic user interface 12 having a liquid crystal display ("LCD") 16 with touch screen capability, a footswitch interface controller 18 disposed within a body 19 of system 10, a force feedback driver 20 disposed within body 19, and a foot controller 26. Controller 18 is a computer and is preferably a microcontroller. Driver 20 is preferably a variable current source driver. A surgical cassette is operatively coupled to system 10 via cassette receiving area 27 to manage the fluidics of system 10 in the conventional manner. As mentioned above, a series of handpieces are operatively coupled to system 10, and/or its surgical cassette, during ophthalmic surgery, typically via conventional flexible plastic tubing fluidly coupled with the surgical cassette and/or electronic cabling operatively coupled to one or more of ports 29. Exemplary handpieces utilized in anterior segment ophthalmic surgery include an irrigation handpiece, an irrigation/aspiration handpiece, an ultrasonic handpiece, and/or a diathermy handpiece. A preferred ultrasonic handpiece is a phacoemulsification handpiece. Exemplary handpieces utilized in posterior segment ophthalmic surgery include an extrusion handpiece, an infusion cannula, a victrectomy probe, microsurgical scissors, and/or a diathermy handpiece.

Figure 3:
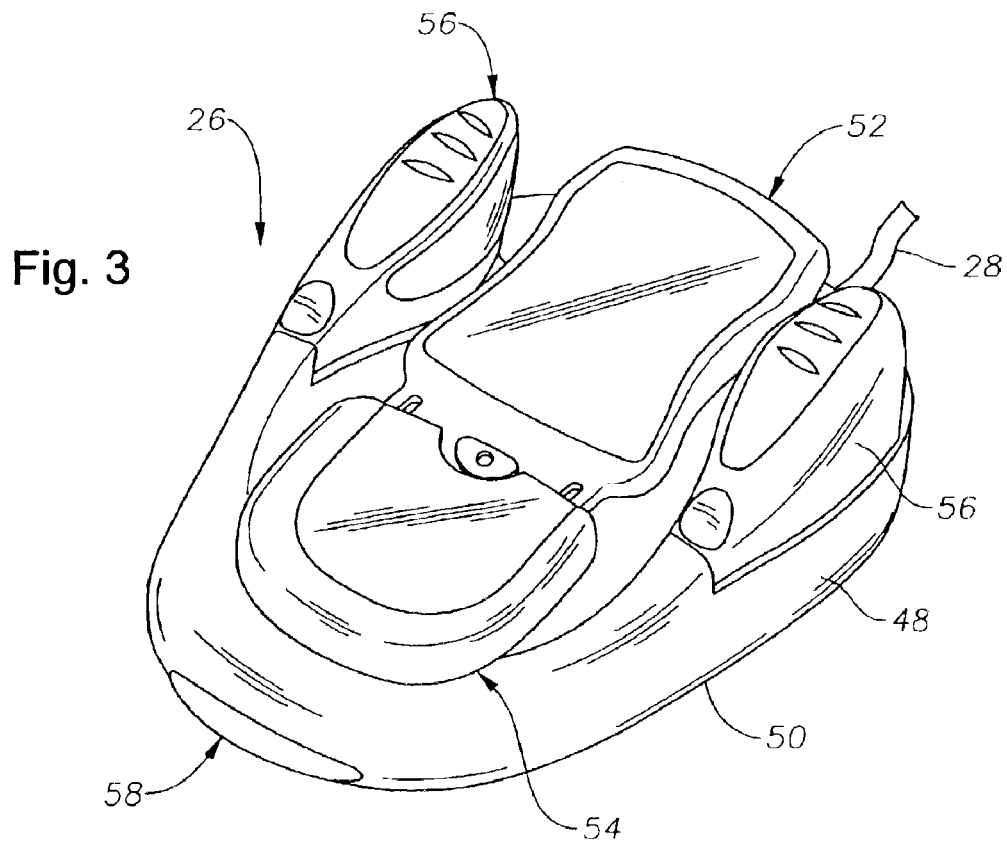
FIG. 3 is perspective view of a preferred embodiment of the foot controller of FIGS. 1–2.
Figure 4:
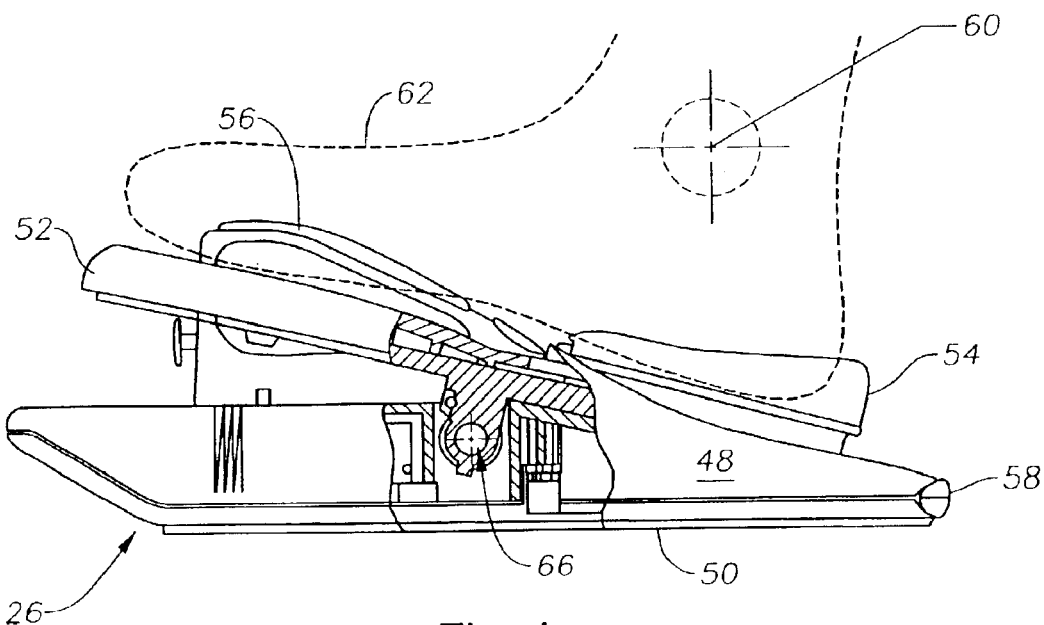
FIG. 4 is a side, partially cut away view of the foot controller of FIG. 3 in a fully undepressed position.
Figure 5:
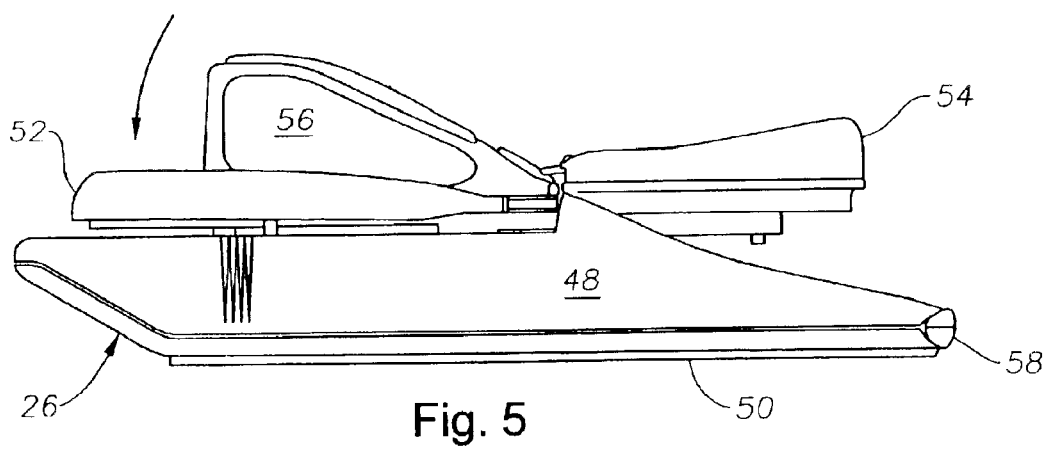
FIG. 5 is a side view of the foot controller of FIG. 3 in a fully depressed position.

As shown best FIGS. 3–5, foot controller 26 has a body 48 with a base 50 that supports foot controller 26 on the operating room floor. Body 48 preferably includes a foot pedal or treadle 52, a heel cup 54, and side or wing switches 56, all of which can be made from any suitable material, such as stainless steel, titanium, or plastic. Base 50 may also contain a protective bumper 58 made from a relatively soft elastomeric material. The structure of foot controller 26 is more completely described in co-pending U.S. appplication Ser. No. 10/271,505 filed Oct. 16, 2002, which is incorporated herein by reference.

Foot pedal 52 and heel cup 54 are rotationally coupled to body 48 at a shaft 66 of foot controller 26. Foot pedal 52 may be depressed using the upper portion of a surgeon's foot to move from a fully undepressed position as shown in FIGS. 3–4, to a fully depressed position as shown in FIG. 5. Ankle axis of rotation 60 of foot 62 is preferably located behind shaft 66. Although not shown in FIGS. 3–5, foot controller 26 may be designed so that only foot pedal 52, and not heel cup 54, rotates about shaft 66, if desired. Foot pedal 52 is used by the surgeon to provide proportional control to certain functions of microsurgical system 10. By way of example, depending on the operating mode of system 10, foot pedal 52 may be used to provide proportional control of vitrectomy probe cut rate, vitrectomy probe aspiration vacuum, ultrasound handpiece power, or ultrasound handpiece aspiration flow rate.

As shown in best in FIG. 2, foot controller 26 preferably also includes a force feedback motor 30 and an encoder 32. Motor 30 is mechanically coupled to shaft 66 via a conventional gear assembly (not shown). Motor 30 is driven by a signal generated by force feedback driver 20 and controlled by footswitch interface controller 18. Encoder 32 is preferably an optical encoder. Encoder 32 monitors the number of rotations of the shaft of motor 30. Encoder 32 includes position detect logic 33 capable of transforming the number of rotations of the shaft of motor 30 into the rotational displacement of foot pedal 52. One or more foot pedal return springs 34 are also coupled to shaft 66. Springs 34 and motor 30 combine to provide a torque or force that resists actuation of foot pedal 52 by a surgeon's foot. Switches 36, 38, and 40 detect and signal controller 18 upon the failure of spring 34, upon the tilting of foot controller 26 off its base 50, and when foot pedal 52 is in a fully undepressed position, respectively. Foot controller 26 may be made using conventional technology. Foot controller 26 is electrically coupled to microsurgical system 10 via electronic cable 28.

Figure 6:
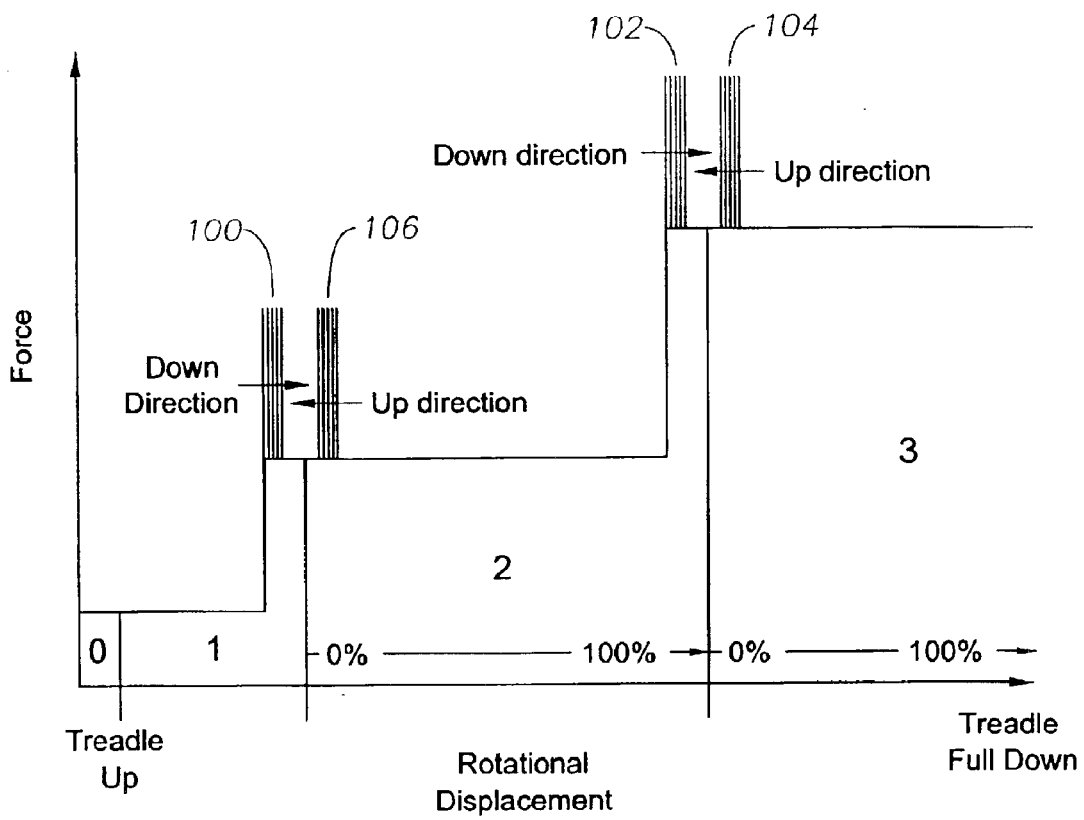
FIG. 6 schematically illustrates the resistive force felt by a surgeon's foot as it presses on the foot pedal of the foot controller of FIG. 3 as a function of the rotational displacement of the foot pedal according to a preferred embodiment of the present invention.

FIG. 6 schematically illustrates the resistive force felt by a surgeon's foot as it presses on foot pedal 52 to control various surgical parameters during operation of microsurgical system 10 as a function of the rotational displacement of foot pedal 52. As shown in the preferred embodiment of FIG. 6, foot controller 26 has a range of motion between a first position where foot pedal 52 is in a fully undepressed position and a second position where foot pedal 52 is in a fully depressed position. This range of motion is preferably separated into multiple sub-ranges or areas, each of which is indicative of a surgical mode of system 10. For an exemplary phacoemulsification handpiece operatively coupled to system 10, the preferred areas are: 0 (no active surgical mode); 1 (fixed amount of irrigation flow provided to handpiece); 2 (fixed amount of irrigation flow provided to handpiece+proportional (0–100%) control of aspiration flow provided to handpiece); and 3 (fixed amount of irrigation flow provided to handpiece+proportional (0–100%) control of aspiration flow provided to handpiece+proportional (0–100%) control of ultrasound power provided to handpiece). Of course, different numbers of areas, as well as different surgical modes, may be assigned for different microsurgical systems other than system 10 and/or different handpieces operatively coupled to system 10. As shown in FIG. 6, foot controller 26 preferably has two detents 100 and 102 as foot pedal 52 is moved in a downward direction, and two detents 104 and 106 as foot pedal 52 is moved in an upward direction. Of course, more or less detents, or different detent locations, may be utilized, if desired.

Figure 7:
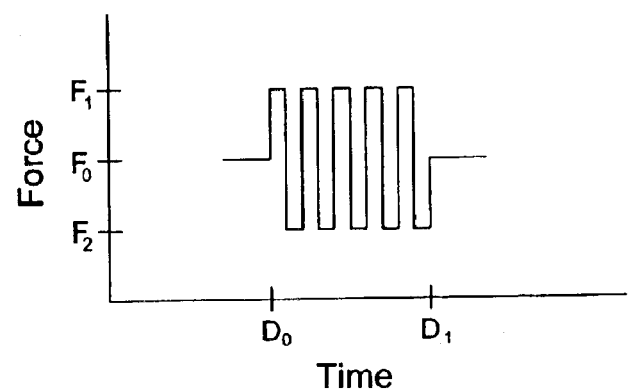
FIG. 7 schematically illustrates a modulating detent of the foot controller of FIG. 3 according to a preferred embodiment of the present invention.
Figure 8:
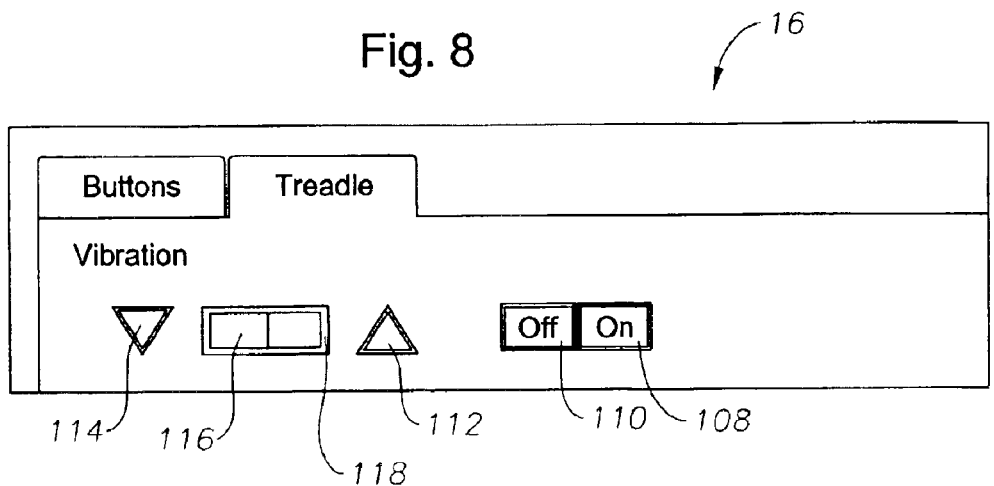
FIG. 8 shows a preferred embodiment of a touch screen display of the microsurgical system of FIG. 1 used to customize the modulating detent of FIG. 5.

As shown in FIGS. 7–8, one or more of detents 100 through 106 may be a modulating detent. More specifically, the resistance, or resistive force or torque, that a surgeon feels against his or her foot as it presses on foot pedal 52 is preferably varied from a first value of amplitude $F_0$ at the beginning $D_0$ of the detent to values of amplitude between a second value of amplitude $F_1$ and a third value of amplitude $F_2$ at a desired frequency throughout the entire detent. At the end $D_1$ of the detent, the resistance preferably returns to the first value of amplitude $F_0$. This modulating detent is significantly different from a conventional foot switch detent, in which the surgeon feels a constant, increased resistance against his or her foot as he or she continues to move the foot pedal of the foot controller from the beginning to the ending of the detent. The modulating detent of the present invention is preferably accomplished by using force feedback driver 20 to vary the electrical signal to force feedback motor 30 so that the opposing torque provided to shaft 66 varies while foot pedal 52 is between the beginning $D_0$ of the detent and the end $D_1$ of the detent. Of course, encoder 32 and position detect logic 33 provide the current rotational displacement of foot pedal 52 to footswitch controller 18, and controller 18 instructs driver 20 on how to appropriately vary the electrical signal to motor 30.

The surgeon or nurse may use touch screen display 16 of system 10 to customize the feel of detents 100 through 106. For example, the surgeon may touch button 108 to activate modulation on all detents 100 through 106, and the surgeon may touch button 110 to deactivate modulation on all detents 100 through 106. As another example, a surgeon may increase the frequency of modulation of all detents 100 through 106 by touching scroll up arrow 112, and the surgeon may decrease the frequency of modulation of all detents 100 through 106 by touching scroll down arrow 114. As the frequency of modulation of the detents is changed, the current frequency is qualitatively displayed by the position of scrolling bar 116 within bar display 118. In addition, the surgeon or nurse may also change the frequency of modulation of detents 100 through 106 by using a mouse connected to user interface 12 to "click and drag" scrolling bar 116 within bar display 118. The absolute value of the difference in the amplitudes $F_1$ and $F_2$ of the resistance felt by a surgeon's foot, as well as the minimum and maximum values for the frequency of modulation of the detents, is preferably hard coded within footswitch controller 18. The preferred value of such minimum and maximum values for the frequency of modulation are about 30 Hz to about 150 Hz. Alternatively, these values could be customized by the surgeon or the nurse using touch screen display 16. In addition, the resistance that a surgeon feels against his or her foot may be modulated between $F_0$ and $F_1$, between $F_0$ and $F_2$, or with some other varying pattern, if desired. Preferably, the pattern of modulation is hard coded within footswitch controller 18. Alternatively, a surgeon or nurse could select from multiple modulation patterns, or customize a modulation pattern, using touch screen display 16. The duration of each of detents 100 through 106 is preferably about 100 milliseconds.

From the above, it may be appreciated that the present invention provides a surgeon with an improved detent in foot controllers used in the operation of microsurgical systems. The present invention eliminates the stiffness felt by the surgeon when the surgeon moves the foot pedal of a foot controller through a conventional detent.

The present invention is illustrated herein by example, and various modifications may be made by a person of ordinary skill in the art. For example, graphic user interface 12 may be used to set a different frequency of modulation for different detents of foot controller 26. In addition, although the modulating detents of the present invention have been described above in connection with a foot pedal 52 having a generally vertical range of motion, the modulating detents of the present invention are applicable to a foot pedal having a generally horizontal range of motion or a range of motion with a different orientation other than vertical or horizontal.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of operating a foot controller of a microsurgical system, comprising the steps of:
    providing a microsurgical system, said system comprising:
        a computer; and
        a foot controller operatively coupled to said computer, said foot controller having a foot pedal with a range of motion, said range of motion having a first area indicative of a first surgical mode of said microsurgical system and a second area indicative of a second surgical mode of said microsurgical system, said first and second areas separated by a detent; and
    using said computer to modulate said detent by varying a resistance felt by a user's foot as said foot presses on said foot pedal, wherein said varying of said resistance comprises increasing said resistance a first time, decreasing said resistance, and increasing said resistance a second time within said detent.

2. The method of claim 1 wherein said varying of said resistance occurs at a given frequency from the beginning of said detent to an end of said detent.

3. The method of claim 2 wherein said frequency may be selected by said user.

4. A method of operating a foot controller of a microsurgical system, comprising the steps of:
    providing a microsurgical system, said system comprising:
        a computer;
        a foot controller operatively coupled to said computer, said foot controller having a foot pedal with a range of motion and a shaft defining an axis of rotation, said range of motion having a first area indicative of a first surgical mode of said microsurgical system and a second area indicative of a second surgical mode of said microsurgical system, said first and second areas separated by a detent; and
        a force feedback motor mechanically coupled to said shaft;
    using said force feedback motor to apply a first torque to said shaft that opposes a second torque applied to said shaft by a user's foot as said foot presses on said foot pedal; and
    using said computer to modulate said detent by varying said first torque, wherein said varying of said first torque comprises increasing said first torque a first time, decreasing said first torque, and increasing said first torque a second time within said detent.

5. The method of claim 4 wherein said varying of said first torque occurs at a given frequency from the beginning of said detent to an end of said detent.

6. The method of claim 5 wherein said frequency may be selected by said user.

7. A method of operating a foot controller of a microsurgical system, comprising the steps of:
    providing a microsurgical system, said system comprising:
        a computer; and
        a foot controller operatively coupled to said computer, said foot controller having a foot pedal with a range of motion, said range of motion having a first area indicative of a first surgical mode of said microsurgical system and a second area indicative of a second surgical mode of said microsurgical system, said first and second areas separated by a detent; and
    using said computer to modulate said detent by varying a resistance felt by a user's foot as said foot presses on said foot pedal, wherein said varying of said resistance comprises decreasing said resistance a first time, increasing said resistance, and decreasing said resistance a second time within said detent.

8. The method of claim 7 wherein said varying of said resistance occurs at a given frequency from the beginning of said detent to an end of said detent.

9. The method of claim 8 wherein said frequency may be selected by said user.

10. A method of operating a foot controller of a microsurgical system, comprising the steps of:
    providing a microsurgical system, said system comprising:

a computer;

a foot controller operatively coupled to said computer, said foot controller having a foot pedal with a range of motion and a shaft defining an axis of rotation, said range of motion having a first area indicative of a first surgical mode of said microsurgical system and a second area indicative of a second surgical mode of said microsurgical system, said first and second areas separated by a detent; and a force feedback motor mechanically coupled to said shaft;

using said force feedback motor to apply a first torque to said shaft that opposes a second torque applied to said shaft by a user's foot as said foot presses on said foot pedal; and using said computer to modulate said detent by varying said first torque, wherein said varying of said first torque comprises decreasing said first torque a first time, increasing said first torque, and decreasing said first torque a second time within said detent.

11. The method of claim 10 wherein said varying of said first torque occurs at a given frequency from the beginning of said detent to an end of said detent.

12. The method of claim 11 wherein said frequency may be selected by said user.

\* \* \* \* \*